US012754153B2

(12) United States Patent
Calleri

(10) Patent No.: US 12,754,153 B2
(45) Date of Patent: Oct. 6, 2026

(54) METHOD AND SYSTEM FOR DETERMINING PHYSICAL PROPERTIES OF ROCKY FORMATIONS

(71) Applicant: Geolog S.r.l., San Giuliano Milanese (IT)

(72) Inventor: Antonio Calleri, San Giuliano Milanese (IT)

(73) Assignee: Geolog S.r.l., San Giuliano Milanese (IT)

( * ) Notice: Subject to any disclaimer, the term of this patent is extended or adjusted under 35 U.S.C. 154(b) by 967 days.

(21) Appl. No.: 18/079,920

(22) Filed: Dec. 13, 2022

(65) Prior Publication Data

US 2023/0184702 A1 Jun. 15, 2023

(30) Foreign Application Priority Data

Dec. 13, 2021 (IT) ........................ 102021000031214

(51) Int. Cl.
*G01N 23/223* (2006.01)
*G01N 33/24* (2006.01)

(52) U.S. Cl.
CPC ......... *G01N 23/223* (2013.01); *G01N 33/241* (2013.01); *G01N 2223/076* (2013.01); *G01N 2223/616* (2013.01)

(58) Field of Classification Search
CPC ..... G01V 99/00; G01N 23/223; G01N 33/241
USPC ........................................................... 702/6
See application file for complete search history.

(56) References Cited

U.S. PATENT DOCUMENTS 10,657,441 B2 * 5/2020 Dursun ................... E21B 44/02
2021/0089897 A1 * 3/2021 Zhang .................... G06N 3/084

OTHER PUBLICATIONS

Salaheldin Elkatatny, "Real-Time Prediction of Rate of Penetration in S-Shape Well Profile Using Artificial Intelligence Models", Date published: Jun. 21, 2020 (Year: 2020).*

* cited by examiner

*Primary Examiner* — John H Le

(57) ABSTRACT

Method for determining physical properties of rocky formations, comprising: training a first artificial intelligence system (AI1) on a first training dataset (TR1). Said first training dataset (TR1) comprises independent variables (V1), associated with one or more rocky formations, comprising at least one of X-ray fluorescence (XRF) measurements, X-ray diffraction (XRD) measurements, and gamma-ray measurements. The independent variables (V1) further comprise one or more drilling parameters. Said first training dataset (TR1) comprises one or more dependent variables (V2), comprising one or more physical properties of said one or more rocky formations. Said first training dataset (TR1) is obtained from one or more training wells. Said method further comprises: determining operating data (OP), associated with a drilling of an operating well and comprising values of XRF and/or XRD measurements and values of said one or more drilling parameters (DP); executing a processing operation, wherein values of one or more of said one or more physical properties (PP) of a rocky formation crossed by said operating well are computed on the basis of said operating data (OP) by means of at least said first artificial intelligence system (AI1).

11 Claims, 3 Drawing Sheets

FIG. 3
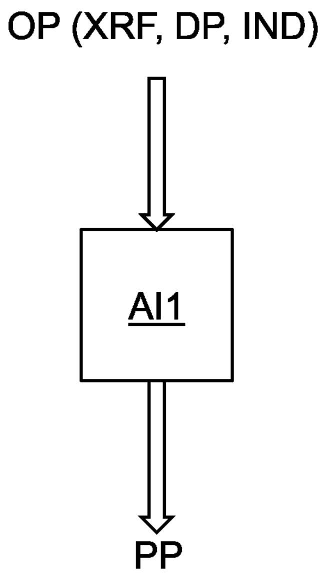
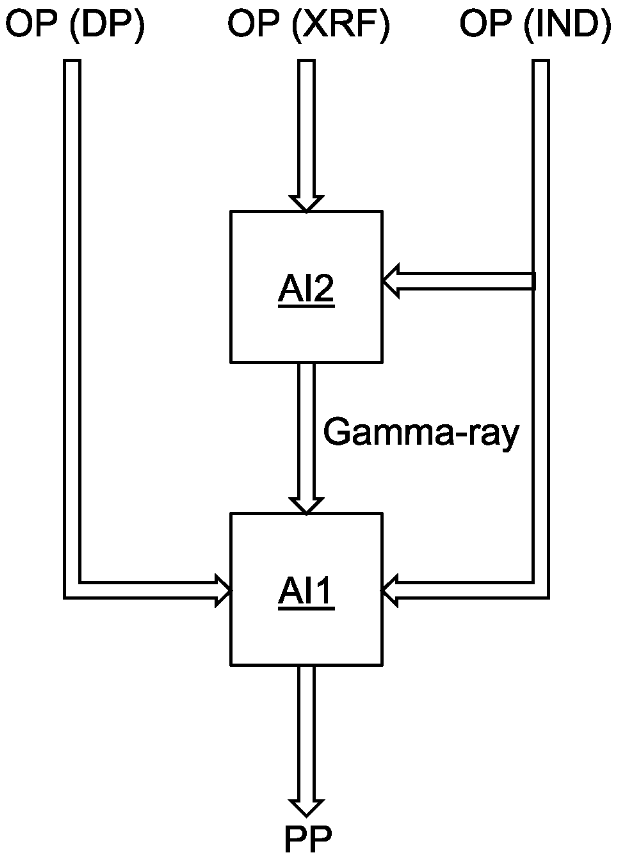
FIG. 4

METHOD AND SYSTEM FOR DETERMINING PHYSICAL PROPERTIES OF ROCKY FORMATIONS

RELATED APPLICATIONS

This application claims the benefit of priority of Italian Patent Application No. 102021000031214 filed on Dec. 13, 2021, the contents of which are incorporated herein by reference in their entirety.

FIELD AND BACKGROUND OF THE INVENTION

The present invention relates to a method for determining physical properties of rocky formations.

The present invention also relates to a system for determining physical properties of rocky formations.

In particular, the present invention is applicable to rocky formations in the subsoil, the physical properties of which are determined/predicted during drilling activities.

Knowing the physical properties of rocky formations (sometimes also referred to as “geomechanical parameters”) is very important for reservoir modelling.

By way of example, the physical properties may comprise Young’s modulus, Poisson’s ratio, and uniaxial compressive strength (UCS).

Typically, such parameters significantly affect several aspects of drilling operations (e.g. well stability and drilling speed), reservoir characterization (compaction, fractured zones, fracture development) and reservoir development (e.g. productivity).

The physical properties of a hydrocarbon reservoir are conventionally assessed on the basis of core logging, sonic logging and/or density logging operations.

Laboratory core analysis is considered the most precise and accurate method for determining the physical properties of a rocky formation. However, this type of analysis is very expensive and time-consuming. For this reason, such analyses are not universally adopted in the industry.

Additionally or alternatively, borehole well logs can provide continuous measurements from which it is possible to calculate approximations to the physical properties of interest. However, these are costly technologies that are not applicable to particular contexts like highly deviated wells or wells having very rough or uneven walls.

The Applicant observes that borehole well logs are typically used for taking measurements within the well by means of probes containing sensors and instruments capable of measuring certain physical properties of the well and of the rocks crossed by it. These measurements can be taken in real time by using tools referred to as MWD (Measurement While Drilling) and LWD (Logging While Drilling). With this technology, the measuring tool is positioned directly on the drill string or in proximity thereto. The measured properties are sent to the surface via pressure impulses that propagate in the mud and, at the same time, are recorded in a memory that can be read when the drill string is extracted from the well. Borehole well logs may also be of the wireline type. In this log type, the measuring tool is inserted in the well by means of a cable. In most wireline logs, data are acquired continuously as the tool moves.

Systems based on artificial intelligence are also available, which permit determining some physical properties, like Poisson’s ratio, uniaxial compressive strength (UCS) and confined compressive strength (CCS).

In this frame, the Applicant felt the need for creating a technique that would allow the physical properties of a rocky formation to be determined in a simple, sufficiently economical and reliable manner.

In particular, the Applicant’s goal was to provide a technique that would allow the physical properties of rocky formations to be determined on the basis of so-called surface logging data.

The Applicant observes that the data acquired by surface logging are made available in real time at mobile containers/laboratories installed near the well. Such data are used for:

- describing the lithologies encountered by the drill bit during the drilling operation by characterizing rock fragments called “cuttings”, brought to the surface by the drilling mud, and determining the presence of any hydrocarbons;
- monitoring the progress of the drilling process by recording the drilling parameters and the main events occurring during the drilling process, e.g. well stability problems or kick detection. The recorded drilling parameters may be, for example, the weight applied to the bit (Weight On bit, WOB), the drilling rate (Rate Of Penetration, ROP) and the revolution speed (Rotation Per Minute, RPM);
- monitoring the drilling mud and the presence of any gases which might, during the return phase, cause catastrophic events;

Surface logging data may also comprise more advanced analyses aimed at providing a more in-depth characterization of the encountered lithologies, the reservoir and the drilling mud. Such analyses may comprise, for example, gas type characterization, XRF and XRD analyses on cuttings, and/or isotopic analyses.

The Applicant observes that, although the invention does not lead to attaining actual real-time results, the system’s output is nevertheless provided in “quasi real-time” conditions, which are perfectly compatible with industrial requirements.

SUMMARY OF THE INVENTION

In accordance with a first aspect, the present invention concerns a method for determining physical properties of rocky formations.

Preferably, the method comprises training a first artificial intelligence system.

Preferably, the first artificial intelligence system is trained on a first training dataset.

Preferably, said first training dataset comprises independent variables.

Preferably, said independent variables are associated with one or more rocky formations.

Preferably, said independent variables comprise X-ray fluorescence (XRF) measurements.

Preferably, said independent variables comprise X-ray diffraction (XRD) measurements.

Preferably, said independent variables comprise one or more drilling parameters.

Preferably, said first training dataset comprises one or more dependent variables.

Preferably, said dependent variables comprise one or more physical properties of said one or more rocky formations.

Preferably, said first training dataset is obtained from one or more training wells.

Preferably, said method comprises determining operating data associated with a drilling of an operating well.

Preferably, said operating data comprise values of XRF measurements.

Preferably, said operating data comprise values of XRD measurements.

Preferably, said operating data comprise values of said one or more drilling parameters.

Preferably, the method comprises executing a processing operation, wherein values of one or more of said one or more physical properties of a rocky formation crossed by said operating well are computed.

Preferably, said values of one or more of said one or more physical properties are computed on the basis of said operating data.

Preferably, said values of one or more of said one or more physical properties are computed by means of at least said first artificial intelligence system.

In accordance with a second aspect, the present invention concerns a system for determining physical properties of rocky formations.

Preferably, said system comprises a processor.

Preferably, said system comprises an input interface coupled to said processor.

Preferably, said system comprises an output interface coupled to said processor.

Preferably, a first artificial intelligence system is loaded in said processor.

Preferably, said first artificial intelligence system is trained on a first training dataset.

Preferably, said first training dataset is associated with training wells.

Preferably, said first training dataset comprises independent variables.

Preferably, said independent variables comprise X-ray fluorescence (XRF) measurements.

Preferably, said independent variables comprise X-ray diffraction (XRD) measurements.

Preferably, said independent variables comprise one or more drilling parameters.

Preferably, said first training dataset comprises one or more dependent variables.

Preferably, said one or more dependent variables comprise one or more physical properties of a rocky formation.

Preferably, said first training dataset has been measured or determined while drilling training wells.

Preferably, said processor is configured for acquiring, via said input interface, operating data associated with a drilling of an operating well.

Preferably, said operating data comprise values of XRF measurements.

Preferably, said operating data comprise values of XRD measurements.

Preferably, said operating data comprise values of said one or more drilling parameters.

Preferably, said processor is configured for executing a processing operation, wherein values of one or more of said one or more physical properties of a rocky formation crossed by said operating well are computed.

Preferably, said values of one or more of said one or more physical properties are computed on the basis of said operating data.

Preferably, said values of one or more of said one or more physical properties are computed by means of said first artificial intelligence system.

Preferably, said processor is configured for generating and outputting, via said output interface, one or more output signals.

Preferably, said one or more output signals contain the computed values of one or more of said one or more physical properties of a rocky formation crossed by said operating well.

In accordance with one or more of the above aspects, the present invention may comprise one or more of the following preferred features.

Preferably, said one or more physical properties comprise a static Young modulus.

Preferably, said one or more physical properties comprise a dynamic Young modulus.

Preferably, said one or more physical properties comprise a static shear modulus (Shear modulus static).

Preferably, said one or more physical properties comprise a dynamic shear modulus (Shear modulus dynamic).

Preferably, said one or more physical properties comprise a static elastic modulus (Bulk modulus static).

Preferably, said one or more physical properties comprise a dynamic elastic modulus (Bulk modulus dynamic).

Preferably, said one or more physical properties comprise a uniaxial compressive strength (UCS).

Preferably, said one or more physical properties comprise a static Poisson's ratio.

Preferably, said one or more physical properties comprise a dynamic Poisson's ratio.

Preferably, said one or more physical properties comprise a primary wave velocity (P wave velocity).

Preferably, said one or more physical properties comprise a secondary wave velocity (S wave velocity).

Preferably, said one or more physical properties comprise an ultimate tensile strength.

Preferably, said one or more physical properties comprise a coefficient of friction.

Preferably, said one or more physical properties comprise a cohesion.

Preferably, said one or more physical properties comprise Lame's first parameter, $\lambda$.

Preferably, said one or more physical properties comprise Lame's second parameter, $\mu$.

Preferably, said one or more physical properties comprise a porosity.

Preferably, said one or more physical properties comprise a density.

Preferably, said one or more drilling parameters comprise a vertical force acting upon a drill bit used for drilling said operating well (Weight On Bit, WOB).

Preferably, said one or more drilling parameters comprise a rate of penetration (ROP) into the subsoil while drilling said operating well.

Preferably, said one or more drilling parameters comprise a revolution speed of the drill bit (Rotation Per minute, RPM).

Preferably, said one or more drilling parameters comprise a torque acting upon the drill bit (Torque).

Preferably, said one or more drilling parameters comprise a pressure in the drilling mud supply line or "flowline" (Standpipe Pressure, SPP).

Preferably, said one or more drilling parameters comprise a vertical force (weight) acting upon the hook to which the equipment supporting the drill bit is hung (Weight On Hook, WOH).

Preferably, said one or more drilling parameters comprise a rate of flow of the drilling mud entering the hydraulic mud circuit (Flow IN).

Preferably, said one or more drilling parameters comprise a rate of flow of mud exiting the annulus (Flow OUT).

Preferably, said one or more drilling parameters comprise a pressure of one or more pumps for drilling mud circulation (Pump Pressure).

Preferably, said one or more drilling parameters comprise one or more properties of the drilling mud.

Preferably, said one or more drilling parameters comprise a parameter associated with a drilling mud flow detection device and representative of a degree of opening/inclination of a flow paddle belonging to said device and configured for intercepting said mud flow and changing its own angle as a function of the rate of said flow.

Preferably, said one or more drilling parameters comprise a bit size (BS).

Preferably, said one or more drilling parameters comprise a bit position (BP).

Preferably, said one or more drilling parameters comprise a bit type.

Preferably, said one or more drilling parameters comprise a drilling depth.

Preferably, said one or more drilling parameters comprise data describing the gas extracted from the drilling mud returning to the surface (Mud gas data).

Preferably, the independent variables of said first training dataset comprise gamma radiation values.

Preferably, said method comprises training a second artificial intelligence system.

Preferably, said second artificial intelligence system is trained on a second training dataset.

Preferably, said second training dataset comprises at least one independent variable.

Preferably, said at least one independent variable comprises values of XRF measurements concerning one or more rocky formations.

Preferably, said at least one independent variable comprises values of XRD measurements concerning one or more rocky formations.

Preferably, said second training dataset comprises at least one dependent variable.

Preferably, said at least one dependent variable comprises gamma radiation values for said one or more rocky formations.

Preferably, said operating data comprise values of XRF measurements concerning said operating well.

Preferably, said operating data comprise values of XRD measurements concerning said operating well.

Preferably, said second training dataset is associated with one or more test wells.

Preferably, said method comprises computing gamma radiation values for said operating well.

Preferably, said gamma radiation values are computed on the basis of XRF measurements concerning said operating well.

Preferably, said gamma radiation values are computed on the basis of XRD measurements concerning said operating well.

Preferably, said gamma radiation values are computed by means of said second artificial intelligence system.

Preferably, in said processing operation, the values of said one or more physical properties of said rocky formation crossed by said operating well are computed by means of said first artificial intelligence system on the basis of the gamma radiation values computed for said operating well.

Preferably, in said processing operation, the values of said one or more physical properties of said rocky formation crossed by said operating well are computed by means of said first artificial intelligence system on the basis of the values of said one or more drilling parameters computed for said operating well.

Preferably, the values of said one or more physical properties are computed by said first artificial intelligence system.

Preferably, said physical properties are divided into a first group and a second group.

Preferably, the physical properties of the first group are computed by the first artificial intelligence system.

Preferably, the physical properties of the second group are computed by executing a further processing step, on the basis of one or more independent variables and/or one or more physical properties of the first group.

Preferably, the values of physical properties computed by the first artificial intelligence system are computed using a single artificial intelligence model.

Preferably, said first artificial intelligence system comprises one or more artificial intelligence subsystems, each one dedicated to a subset of the physical properties computed by said first artificial intelligence system.

Preferably, the independent variables of the first training dataset comprise a lithological indication of said one or more rocky formations of one or more training wells.

Preferably, said operating data comprise a lithological indication of one or more rocky formations of the operating well.

Preferably, one or more of said one or more dependent variables included in said first training dataset are computed on the basis of sonic logs concerning said training wells.

Preferably, one or more of said one or more dependent variables included in said first training dataset are computed on the basis of density logs concerning said training wells.

BRIEF DESCRIPTION OF THE SEVERAL VIEWS OF THE DRAWINGS

Further features and advantages will become more apparent in the light of the following detailed description of some preferred, but non-limiting, embodiments of the invention. Such description is provided herein with reference to the annexed drawings, which are also supplied merely by way of non-limiting example, wherein:

FIG. 3 schematically shows an operating phase of the artificial intelligence system of FIG. 1, in accordance with one embodiment of the invention;

FIG. 4 schematically shows an operating phase of the artificial intelligence systems of FIGS. 1 and 2, in accordance with one embodiment of the invention;

DESCRIPTION OF SPECIFIC EMBODIMENTS OF THE INVENTION

Figure 5:
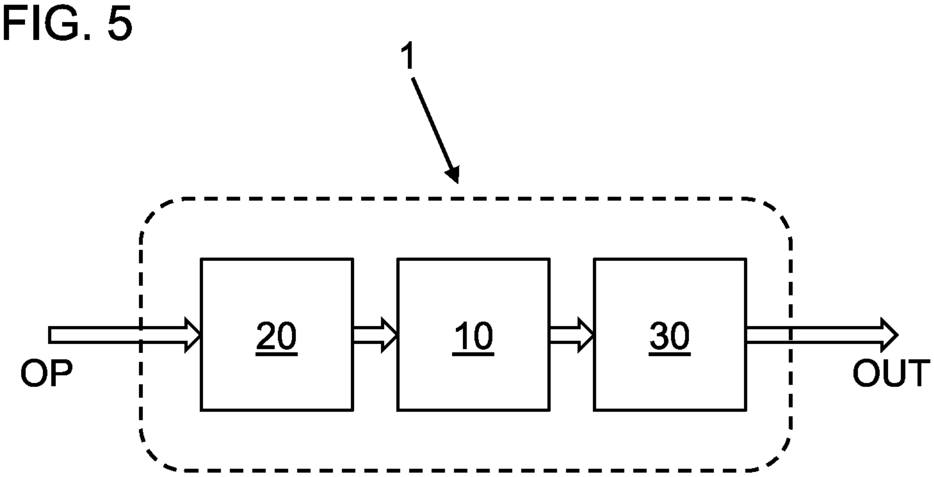
FIG. 5 shows a simplified block diagram of a system according to the present invention.

With reference to FIG. 5, numeral 1 designates as a whole a system for determining physical properties of rocky formations. In particular, the system 1 (and the method implemented by it) are aimed at determining mechanical (or "geomechanical") properties of rocky formations.

The system 1 is advantageously employed at drilling wells, typically created in order to find/reach a reservoir in the subsoil (e.g. a hydrocarbon reservoir).

Hereafter the term "operating well" will indicate a drilling well of this kind.

The operating well is drilled by using per se known technology and equipment. In brief, a drill bit is rotatably moved about its longitudinal axis (which is substantially parallel to the direction of advancement of the bit in the subsoil) in order to excavate the soil and perform the drilling.

Residues of crushed rock (cuttings) are brought to the surface by a flow of mud (referred to as drilling mud), which is pumped from the surface towards the drill bit through the pipes that support it, and which then returns to the surface through the so-called annulus. As will become apparent below, such cuttings can be analyzed in order to obtain useful information about the well and the subsoil.

Referring back to the system 1, it comprises an input interface 10.

Via the input interface 10, operating data OP are received by the system 1.

The operating data OP may comprise values of XRF (X-ray fluorescence) measurements taken on rock samples. The rock samples to be analyzed are taken from the operating well, in particular obtained from the cuttings brought to the surface by the drilling mud.

The values of the XRF measurements may comprise values representative of the presence of specific elements, such as, for example: Silicon, Aluminium, Iron, Potassium, Calcium, Magnesium, Sulphur, Phosphorous, Titanium, Manganese. The presence of these elements can be expressed, for example, in percentage (by volume and/or weight).

The values of the XRF measurements may comprise values representative of the presence of traces of some elements, such as, for example: Chlorine, Arsenic, Copper, Nickel, Vanadium, Molybdenum, Strontium, Lead, Zinc, Zirconium, Rubidium, Thorium, Uranium, Chromium, Cobalt, Niobium, Neodymium, Caesium, Gallium, Gadolinium, Lanthanum, Barium. The presence of these elements can be expressed, for example, in parts per million (ppm).

The values of the XRF measurements may comprise values representative of the presence of some oxides, such as, for example: $SiO_2$, $Al_2O_3$, $Fe_2O_3$, $K_2O$, CaO, MgO, $SO_2$, $P_2O_5$, $TiO_2$, MnO. The presence of these oxides can be expressed, for example, in percentage (by volume and/or weight).

Ratios between the measured quantities of various elements/substances may also be considered, such as, for example: $K_2O/Al_2O_3$, Zr/Nb, $SiO_2/Al_2O_3$, Log ($Fe_2O_3/K_2O$), Log ($SiO_2/Al_2O_3$).

The Applicant observes that, typically, the XRF technology is used in order to directly measure the presence of individual elements, but not the presence of oxides. However, by convention, the reference standards express the major elements in oxide form (%), with the exception of sulphur, which remains expressed as element, still in %. All other minor elements are expressed in ppm. To convert the measured value of an individual element into the corresponding value for an oxide, multiplication factors are used which are given by the ratio between molecular weight and atomic weights.

As concerns the above-mentioned elements and oxides and the ratios between them, those shown herein are merely non-limiting examples. Therefore, the measurements may include readings of substances not listed above.

In addition or as an alternative, the operating data OP may comprise values of XRD (X-ray diffraction) measurements taken on rock samples.

The values of the XRD measurements may comprise values representative of the presence of specific substances, such as, for example, carbonates, silicates, accessory minerals, evaporites, micas and clays.

By way of example, carbonates may comprise: Calcite, Dolomite, Magnesite, Ankerite, Siderite.

By way of example, silicates may comprise: Quartz, Anorthite, Albite, Orthoclase.

By way of example, accessory minerals may comprise: Pyrite, Magnetite.

By way of example, evaporites may comprise: Gypsum, Anhydrite, Halite.

By way of example, micas and clays may comprise: Kaolinite, Illite, Chlorite, Smectite+I/S, Barite, Glauconite, Biotite, Muscovite.

The operating data OP further comprise values of one or more drilling parameters DP. The drilling parameters DP may comprise one or more of:

- a vertical force (weight) acting upon the drill bit used for drilling the operating well (referred to as Weight On Bit, WOB);
- a rate of penetration (ROP) into the subsoil while drilling said operating well;
- a revolution speed of the drill bit (referred to as Rotation Per Minute, RPM);
- a torque acting upon the drill bit (Torque);
- a pressure in the drilling mud supply line or "flowline" (referred to as Standpipe Pressure, SPP);
- a vertical force (weight) acting upon the hook to which the equipment supporting the drill bit is hung (referred to as Weight On Hook, WOH);
- a rate of flow of drilling mud entering the hydraulic mud circuit (referred to as Flow IN);
- a rate of flow of mud exiting the annulus (referred to as Flow OUT);
- a pressure of one or more pumps for drilling mud circulation (referred to as Pump Pressure);
- one or more properties of the drilling mud, e.g. weight, density and/or viscosity;
- a parameter associated with a drilling mud flow detection device and representative of a degree of opening/inclination of a flow paddle belonging to said device and configured for intercepting said mud flow and changing its own angle as a function of the rate of said flow;
- bit size (BS);
- bit position (BP);
- bit type;
- drilling depth;
- data describing the gas extracted from the drilling mud returning to the surface (referred to as Mud gas data).

It should be noted that the drilling parameters DP can be mutually combined and/or modified/processed. Merely by way of example, one may consider the Weight On Bit divided by the cross-sectional area of the drill bit. Other drilling parameters DP may also be normalized or modified differently than described and claimed herein.

In one embodiment, the operating parameters OP may further comprise a lithological indication IND of the rocky formation(s) of the operating well. In practice, such lithological indication IND may include, for example, a geographic/scientific denomination (e.g.: Vaca Muerta Formation; Marcellus shale; Barnett shale, Khuff Formation), a descriptive denomination (e.g.: clay, sandstone, calcareous formation, etc.), or even just a simple identification code (e.g. an alphanumerical one), associated with a corresponding lithological denomination or type.

In one embodiment, the operating parameters OP may also comprise results of measurements taken on cuttings, e.g. by means of one or more of white light (RGB), ultraviolet radiation and infrared radiation, thereby obtaining corresponding absorption spectra of the analyzed fragments.

In one embodiment, the operating parameters OP may also comprise the shape and size of the cuttings.

The samples whereon XRF and/or XRD measurements are to be taken are collected at substantially the same depth to which the drilling parameters OP refer.

In other words, different depth levels are considered, and for each level the XRF and/or XRD measurements are associated with corresponding drilling parameters.

This association can be made, for example, by coupling the measured data (XRF and/or XRD, and drilling parameters DP) with their respective depth.

The same also applies to the lithological indications IND, which are associated with the XRF/XRD measurements and with the drilling parameters on a depth basis.

The system 1 further comprises a processor 10.

The processor 10 is provided with at least one suitably trained artificial intelligence system (which will be further described below).

The processor 10 is configured for computing, based on the operating data OP received via the input interface 10, physical properties PP of the rocky formations encountered by the drill bit.

The values of such physical properties PP are made available through an output interface 30, coupled to the processor 10. In particular, the output interface 30 supplies an output signal OUT that contains the values computed by the processor 10 for the physical properties PP.

Preferably, the physical properties PP comprise one or more of:

- static Young modulus;
- dynamic Young modulus;
- static shear modulus (Shear modulus static);
- dynamic shear modulus (Shear modulus dynamic);
- static elastic modulus (Bulk modulus static);
- dynamic elastic modulus (Bulk modulus dynamic);
- uniaxial compressive strength (UCS);
- static Poisson's ratio;
- dynamic Poisson's ratio;
- primary wave velocity (P wave velocity);
- secondary wave velocity (S wave velocity);
- ultimate tensile strength;
- coefficient of friction;
- cohesion, i.e. that component of shear stress which is independent of friction between particles;
- Lamè's first parameter, $\lambda$;
- Lamè's second parameter, $\mu$;
- porosity;
- density.

The values of the physical properties PP thus obtained can be used, whether by the processor 10 or by other suitably configured devices/apparatuses, for static and/or dynamic reservoir modelling.

The processor 10 is provided with at least a first artificial intelligence system AI1. As will become apparent below (e.g. with reference to FIG. 6), the first artificial intelligence system AI1 can be used for computing the physical properties PP of interest, or even just a part thereof; the remaining ones can then be computed by means of equations known in the literature. It should not be excluded, however, that all the physical properties PP of interest can be computed by the first artificial intelligence system AI1.

In order to obtain the above-described output, the first artificial intelligence system A1 is trained on a first training dataset TR1.

It should be noted that the first training dataset TR1 is obtained from one or more training wells.

Preferably, the training wells do not coincide with the operating well, but have similar characteristics (e.g. they belong to the same geographic area).

The first training dataset TR1 comprises independent variables V1 and dependent variables V2.

The independent variables V1 of the first training dataset TR1 are associated with one or more rocky formations of the training wells, and comprise at least one of:

- X-ray fluorescence (XRF) measurements;
- X-ray diffraction (XRD) measurements;
- gamma-ray measurements (gamma-ray log).

The independent variables V1 of the first training dataset TR1 further comprise one or more drilling parameters.

The XRF, XRD and gamma-ray measurements are carried out in a per se known manner and require no further description.

The drilling parameters included in the independent variables V1 of the first training dataset TR1 may comprise one or more of:

- a vertical force acting upon a drill bit used for drilling one of the training wells (Weight On Bit, WOB);
- a rate of penetration (ROP) into the subsoil while drilling one of the training wells;
- a revolution speed of the drill bit (referred to as Rotation Per minute, RPM);
- a torque acting upon the drill bit (Torque);
- a pressure in the drilling mud supply line or "flowline" (referred to as Standpipe Pressure, SPP);
- a vertical force (weight) acting upon the hook to which the equipment supporting the drill bit is hung (referred to as Weight On Hook, WOH);
- a rate of flow of drilling mud entering the hydraulic mud circuit (referred to as Flow IN);
- a rate of flow of mud exiting the annulus (referred to as Flow OUT);
- a pressure of one or more pumps for drilling mud circulation (referred to as Pump Pressure);
- one or more properties of the drilling mud, e.g. weight, density and/or viscosity;
- a parameter associated with a drilling mud flow detection device and representative of a degree of opening/inclination of a flow paddle belonging to said device and configured for intercepting said mud flow and changing its angle as a function of the rate of said flow;
- bit size (BS);
- bit position (BP);
- bit type;
- drilling depth;
- data describing the gas extracted from the drilling mud returning to the surface (referred to as Mud gas data).
- well diameter; in this regard, the Applicant observes that the well diameter can be measured by means of tools called "caliper logs".

The drilling parameters included in the independent variables V1 of the first training dataset TR1 are computed and stored in a per se known manner, by means of commercially available equipment.

In one embodiment, the independent variables V1 of the first training dataset TR1 may further comprise a lithological indication of the rocky formation(s) of the training well(s), which corresponds to the above-mentioned lithological indication IND included in the operating parameters OP. For training wells, lithological indications are known from previous drillings and analyses.

In one embodiment, the independent variables V1 of the first training dataset TR1 may also comprise results of measurements taken on cuttings, e.g. by means of one or more of white light (RGB), ultraviolet radiation and infrared radiation, thereby obtaining corresponding absorption spectra of the analyzed fragments.

In one embodiment, the independent variables V1 of the first training dataset TR1 may further comprise the shape and size of the cuttings.

The dependent variables V2 of the first training dataset TR1 comprise one or more physical properties of the rocky formations taken into account.

Such physical properties may comprise one or more of:

- static Young modulus;
- dynamic Young modulus;
- static shear modulus (Shear modulus static);
- dynamic shear modulus (Shear modulus dynamic);
- static elastic modulus (Bulk modulus static);
- dynamic elastic modulus (Bulk modulus dynamic);
- uniaxial compressive strength (UCS);
- static Poisson's ratio;
- dynamic Poisson's ratio;
- primary wave velocity (P wave velocity);
- secondary wave velocity (S wave velocity);
- ultimate tensile strength;
- coefficient of friction;
- cohesion, i.e. that component of shear stress which is independent of friction between particles;
- Lamè's first parameter, λ;
- Lamè's second parameter, μ;
- porosity;
- density.

These physical properties are typically computed by one or more of core logging, sonic logging and density logging.

By way of example, in order to compute the Young modulus starting from well logging data, one may consider the equation proposed by Elkatatny, S. et al. ("New approach to optimize the rate of penetration using artificial neural network"—Arabian Journal for Science and Engineering, 43(11), 6297-6304, 2018):

$$lnE_{static}=14.9-0.61*ln(\Delta t_p)-2.18(\Delta t_s)+1.42(ln p_b)$$

where:

- $E_{static}$ is the static Young modulus
- $\Delta t_p$ is the time of propagation of the compression wave, expressed in μsec/ft
- $\Delta t_s$ is the time of propagation of the shear wave, expressed in μsec/ft
- $\rho_b$ is apparent density, expressed in g/cm$^3$.

If the time of propagation of the compression wave is available, but that of the shear wave is unknown, the state of the art provides several equations that correlate such data. For example, the following equation may be used, as proposed by Al-Kattan, W. M. ("Prediction of Shear Wave velocity for carbonate rocks. Iraqi Journal of Chemical and Petroleum Engineering, 16(4), 45-49-2015):

$$Vs=0.699*Vp^{0.969}$$

which correlates compression wave velocity ($v_p$) with shear wave velocity ($V_s$) in carbonate rocks.

The Applicant points out that the above formulae are wholly illustrative and may be replaced with other formulae known in the literature.

Preferably, one or more of the following algorithms may be used for the first artificial intelligence system AI1: random forest, support vector regression, and gradient boosting.

Figure 1:
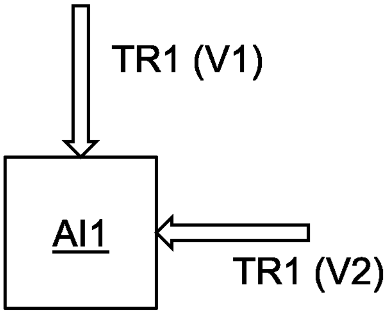
FIG. 1 schematically shows a phase of training a first artificial intelligence system that can be employed in the present invention.

FIG. 1 schematically shows the phase of training the first artificial intelligence system AIL in accordance with the above description.

As aforementioned, the independent variables V1 may comprise X-ray fluorescence (XRF) measurements, X-ray diffraction (XRD) measurements, and gamma-ray measurements.

If training occurs directly with values of XRF and/or XRD measurements, then the first artificial intelligence system AI1 will be able to correlate XRF and/or XRD measurements and drilling parameters (as well as any lithological indications IND), used as independent variables, with the dependent variables consisting of the physical properties of the rocky formations.

If training occurs by means of gamma-ray measurements (gamma-ray log), the processor 10 must be equipped with a second artificial intelligence system AI2.

The second artificial intelligence system AI2 is trained on a second training dataset TR2.

The second training dataset TR2 comprises at least one independent variable V3 and at least one dependent variable V4.

The independent variable V3 comprises values of XRF and/or XRD measurements concerning a rocky formation.

In one embodiment, the at least one independent variable V3 may comprise the lithological indication IND.

The dependent variable V4 comprises gamma-ray emission values for the same rocky formation.

In this way, the second artificial intelligence system AI2 will be able to correlate values of XRF and/or XRD measurements, possibly combined with a lithological indication, with gamma-ray emission values.

Advantageously, the data used as independent variable(s) are associated with the depth from which the analyzed cuttings were collected, so that predictions can be made which concern rocky formations at specific depths along the operating well.

By way of example, one or more of the following algorithms may be used for the second artificial intelligence system AI2: multiple linear regression, random forest, and support vector regression.

The Applicant observes that the second training dataset TR2 is obtained from test wells not coinciding with the operating well, but having similar characteristics, e.g. belonging to the same geographical area as the operating well. In one embodiment, the test wells may coincide, wholly or partly, with the training wells.

In one embodiment, equations known in the literature may be used in the place of the second artificial intelligence system AI2, which permit computing the gamma ray starting from XRF/XRD measurements. By way of example, the following equation can be used (Ellis and Singer, 2007):

$$\text{Chemical Gamma}=(K_2O\times 13.55)+(Th\times 3.93)+(U\times 8.08)$$

where:

- Chemical Gamma is gamma-ray computed from XRF data, measured in API gamma-ray units;
- $K_2O$ represents the concentration (%) of potassium oxide;

Th represents the concentration of thorium in parts per million (ppm);

U represents the concentration of uranium in parts per million (ppm).

Figure 2:
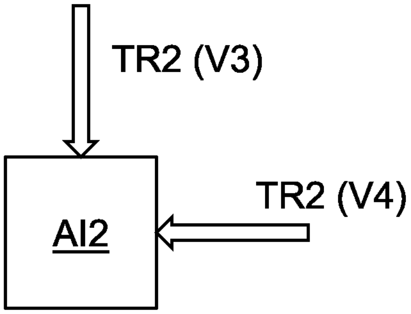
FIG. 2 schematically shows a phase of training a second artificial intelligence system that can be employed in the present invention.

FIG. 2 schematically shows the phase of training the second artificial intelligence system AI2, in accordance with the above description.

In brief, the training phases in accordance with the present invention are carried out as follows:

First artificial intelligence system AI1: the drilling parameters are measured and stored while drilling the training wells; during such drillings, XRF and/or XRD measurements and/or gamma-ray logs are taken; core logging, sonic logging and/or density logging techniques are also applied during such drillings, so as to compute and store values of physical properties of the encountered rocky formations; in addition, information of lithological nature (lithological indications) about the training wells is also stored. The data thus obtained are used for training the first artificial intelligence system AI1. In particular, the drilling parameters and the XRF and/or XRD measurements, or the gamma-ray logs (and possibly any lithological indications IND), constitute the independent variables, while the physical properties constitute the dependent variables.

Second artificial intelligence system AI2: XRF and/or XRD measurements are taken on rocky formations along with, on the same formations, measurements of gamma-ray emissions. These data are used for training the second artificial intelligence system AI2.

FIG. 3 represents the operating phase of the first artificial intelligence system AI1, when it has been trained using, among the independent variables V1 of the first training dataset TR1, values of XRF and/or XRD measurements: the operating data OP, comprising values of XRF and/or XRD measurements and the drilling parameters DP (and any lithological indications IND) of the operating well are inputted to the first artificial intelligence system AI1 (which resides in the processor 10, shown in FIG. 5), which in turn outputs the values of the physical properties PP of the rocky formations of the operating well.

FIG. 4 represents, on the other hand, the operating phase of the first artificial intelligence system AI1 when it has been trained using, among the independent variables V1 of the first training dataset TR1, values of gamma-ray emissions. The operating data OP comprise, as in the previous case, XRF and/or XRD measurements and drilling parameters DP. The XRF and/or XRD measurements are inputted to the second artificial intelligence system AI2, which returns corresponding gamma-ray log values. The latter, together with the drilling parameters DP, are inputted to the first artificial intelligence system AIL which then outputs the values of the physical properties PP of the rocky formations of the operating well.

The operation of the present invention can be summarized as follows:

In all cases, XRF and/or XRD measurements are taken and drilling parameters DP are computed during the operating phase, thereby obtaining operating data OP; optionally, the operating data may also comprise the lithological indication IND;

If the first artificial intelligence system AI1 has been trained on XRF and/or XRD measurements and the same drilling parameters DP, then the operating data OP can be inputted directly to the first artificial intelligence system AI1 to obtain the values of the physical properties of the rocky formations;

If the first artificial intelligence system AI1 has been trained on gamma-ray measurements, then the XRF and/or XRD readings are inputted to the second artificial intelligence system AI2, possibly with the addition of the lithological indication IND, to obtain corresponding gamma-ray log values; the latter, together with the drilling parameters DP, are then inputted to the first artificial intelligence system AI1.

Preferably, the physical properties for which the first artificial intelligence system AI1 can output values during the operating phase are the same physical properties for which values were supplied to the first artificial intelligence system AI1 during the training phase.

As concerns the first artificial intelligence system AI1, many embodiments are possible.

In one embodiment, the values of the physical properties PP are computed by the first artificial intelligence system AI1. In other words, substantially all the output values of the physical properties PP are provided by the first artificial intelligence system AI1 during the operating phase.

In one embodiment, the physical properties PP are divided into a first group and a second group:

the physical properties of the first group are computed directly by the first artificial intelligence system AI1;

the physical properties of the second group are computed by executing a further processing step, on the basis of one or more independent variables and/or one or more physical properties of the first group.

In one embodiment, the values of physical properties computed by the first artificial intelligence system AI1 are computed using a single artificial intelligence model. In other words, a single artificial intelligence model is first trained and then used during the operating phase, receiving as input the operating parameters OP and outputting the values of the physical properties PP of interest (whether computed directly or through said further processing step).

In one embodiment, the first artificial intelligence system AI1 comprises one or more artificial intelligence subsystems S1-S5; each artificial intelligence subsystem is dedicated to a subset of the physical properties computed by the first artificial intelligence system AI1. Each subset may comprise one or more physical properties. For example, each artificial intelligence subsystem S1-S5 (FIG. 6), which will be further described below, is dedicated to computing only one physical property.

Figure 6:
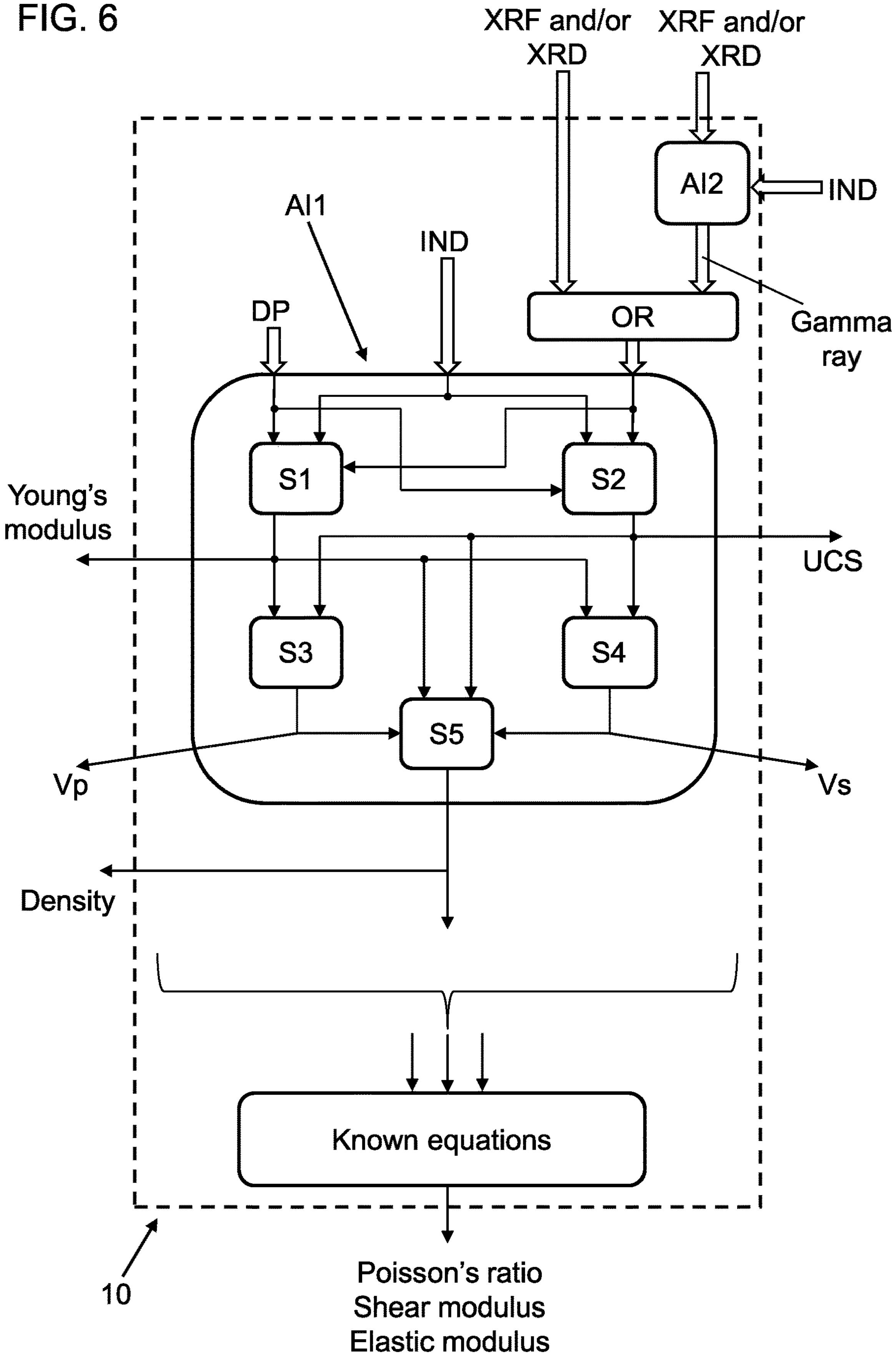
FIG. 6 schematically shows one possible embodiment of an artificial intelligence system employed in the present invention.

FIG. 6 shows an example of embodiment of the first artificial intelligence system AI1 in the operating phase (i.e. already trained). The system is inputted the operating parameters OP (drilling parameters DP, lithological indication IND, XRF and/or XRD measurements—the latter optionally converted into gamma-ray values by the second artificial intelligence system AI2). Based on the operating parameters OP, the first artificial intelligence subsystem S1 computes the Young modulus. Based on the operating parameters OP, the second artificial intelligence subsystem S2 computes the UCS. Young modulus and UCS may be outputted as data of interest and/or used for computing other properties. Based on Young modulus and UCS, the third artificial intelligence subsystem S3 computes the primary wave velocity Vp. Based on Young modulus and UCS, the fourth artificial intelligence subsystem S4 computes the secondary wave velocity Vs. Based on Young modulus, UCS, Vp and Vs, the fifth artificial intelligence subsystem S5 computes the density. Through the additional processing step, e.g. by means of equations that are per se known in the literature, and on the basis of one or more operating parameters OP and/or one or more physical properties computed by the first artificial intelligence system AI1, it is possible to compute one or more of Poisson's ratio, shear modulus and elastic modulus. In the example of FIG. 6:

Young modulus, USC, Vp, Vs and density constitute the first group of physical properties;

Poisson's ratio, shear modulus and elastic modulus constitute the second group of physical properties.

The Applicant observes that the basic concepts of the present invention are also applicable to other implementation examples.

In a first application, for example, during the training phase drilling parameters and wireline gamma-ray measurements are used as independent variables, and physical properties of the rocky formations (computed on the basis of sonic logs and density logs) are used as dependent variables. During the operating phase, the input quantities are the drilling parameters and the wireline gamma-ray measurements, and the output consists of the physical properties of the rocky formations. In this example, the processing operations are carried out in "quasi real-time" mode, because the parameters in use (particularly the wireline gamma-ray measurements) need some time to be acquired and analyzed. The Applicant believes, however, that such time is fully compatible with the industrial and operating requirements of a drilling well.

In a second application, for example, during the training phase drilling parameters and LWD/MWD (Logging While Drilling/Measure While Drilling) gamma-ray measurements are used as independent variables, and physical properties of the rocky formations (computed on the basis of sonic logs and density logs) are used as dependent variables. During the operating phase, the input quantities are the drilling parameters and the LWD gamma-ray measurements, and the output consists of the physical properties of the rocky formations. In this example, the processing operations are carried out substantially in real time, because the parameters in use can be acquired and processed in real time.

In a third application, for example, during the training phase drilling parameters are used as independent variables, and physical properties of the rocky formations (computed on the basis of sonic logs and density logs) are used as dependent variables. During the operating phase, the input quantities are the drilling parameters, and the output consists of the physical properties of the rocky formations. In this example, the processing operations are carried out substantially in real time, because the parameters in use can be acquired and processed in real time.

With reference to FIG. 5, it should be noted that, for simplicity's sake, such figure schematically shows only one processor 10. In real-world applications, however, two or more processors, suitably programmed and managed, may alternatively be used for executing the processing operations described and claimed herein. One or more non-volatile memories may be associated with the processor 10 (or with the processors, if more than one). The memory(ies) may store the parameters useful for the execution of the processing operations in accordance with the embodiments described herein. Generally, the processor 10—along with the associated non-volatile memory(ies)—represents the hardware/software resources that are necessary for computing the values of the physical properties of the rocky formations as a function of the operating data. As aforesaid, the first artificial intelligence system AI1 and, preferably, also the second artificial intelligence system AI2 reside in the processor 10.

The input interface 20 is, preferably, a physical (wired or wireless) connection through which the processor 10 can receive the data necessary for training the first artificial intelligence system AI1 (and, preferably, also the second artificial intelligence system AI2) and/or the data necessary for the prediction phase, i.e. the operating data OP. For example, the input interface 20 may provide a connection to an internal or external storage medium, or to another electronic device, from which the data can be acquired by the processor 10.

The output interface 30 is, preferably, a physical (wired or wireless) connection through which the processor 10 can output the results of the processing operations carried out (i.e. the values of the physical properties of the analyzed rocky formations). For example, the output interface 30 may provide a connection to a display device (not shown) to allow one or more operators to observe such results. In addition or as an alternative, the output interface 30 may provide a connection to a storage medium, in which the results can be stored.

The invention attains important advantages.

First and foremost, the invention permits determining physical parameters of a rocky formation in a simple, sufficiently economical and reliable manner.

In particular, the invention makes it possible to determine physical parameters of rocky formations on the basis of surface logging data.

A further advantage lies in the fact that the invention can provide the requested outputs in "quasi real-time" conditions, which are perfectly compatible with industrial logics and requirements.

What is claimed is:

1. A method for determining physical properties of rocky formations during drilling of an operating well, the method comprising:

training a first artificial intelligence system (AI1) on a first training dataset (TR1) obtained from one or more training wells, said first training dataset (TR1) comprising: independent variables (V1), associated with one or more rocky formations of said one or more training wells, comprising: (i) at least one of X-ray fluorescence (XRF) measurements, X-ray diffraction (XRD) measurements, and gamma-ray measurements taken on cuttings or rocky formations of said one or more training wells, and (ii) one or more drilling parameters acquired during drilling of said one or more training wells;

one or more dependent variables (V2), comprising one or more physical properties of said one or more rocky formations, of said one or more training wells, said one or more dependent variables being depth-correlated with said independent variables;

acquiring, in quasi-real-time during drilling of the operating well, operating data (OP) comprising values of XRF and/or XRD measurements taken on cuttings brought to the surface by drilling mud of said operating well and values of said one or more drilling parameters (DP) of said operating well, said values being depth-correlated;

computing, by said first artificial intelligence system (AI1) based on said operating data (OP), values of one or more physical properties (PP) of a rocky formation crossed by said operating well; and outputting, via an output interface, one or more output signals containing said computed values of said one or more physical properties (PP) for use in at least one of (i) controlling or adjusting at least one of said one or more drilling parameters of said operating well, and (ii) modelling a reservoir crossed by said operating well.

2. The method according to claim 1, wherein said one or more physical properties (PP) comprise one or more of:

static Young modulus;
dynamic Young modulus;
static shear modulus (Shear modulus static);
dynamic shear modulus (Shear modulus dynamic);
static elastic modulus (Bulk modulus static);
dynamic elastic modulus (Bulk modulus dynamic);
uniaxial compressive strength (UCS);
static Poisson's ratio;
dynamic Poisson's ratio;
primary wave velocity (P wave velocity);
secondary wave velocity (S wave velocity);
ultimate tensile strength;
coefficient of friction;
cohesion;
Lamè's first parameter, λ;
Lamè's second parameter, μ;
porosity;
density.

3. The method according to claim 1, wherein said one or more drilling parameters comprise one or more of:

a vertical force acting upon a drill bit (Weight On Bit, WOB);
a rate of penetration (ROP);
a revolution speed of the drill bit (Rotation Per Minute, RPM);
a torque acting upon the drill bit;
a pressure in a drilling mud supply line (Standpipe Pressure, SPP);
a vertical force acting upon a hook to which equipment supporting the drill bit is hung (Weight On Hook, WOH);
a rate of flow of drilling mud entering a hydraulic mud circuit (Flow IN);
a rate of flow of mud exiting an annulus (Flow OUT);
a pressure of one or more pumps for drilling mud circulation (Pump Pressure);
one or more properties of the drilling mud;
a parameter associated with a drilling mud flow detection device representative of a degree of opening or inclination of a flow paddle;
bit size (BS);
bit position (BP);
bit type;
drilling depth;
and data describing gas extracted from drilling mud returning to the surface.

4. The method according to claim 1, wherein the independent variables (V1) of said first training dataset (TR1) comprise gamma radiation measurements, said method further comprising:

training a second artificial intelligence system (AI2) on a second training dataset (TR2) obtained from one or more test wells, said second training dataset (TR2) comprising:

(i) at least one independent variable (V3) comprising values of XRF and/or XRD measurements concerning one or more rocky formations, and (ii) at least one dependent variable (V4) comprising gamma radiation values for said one or more rocky formations;

wherein said operating data (OP) comprise values of XRF and/or XRD measurements concerning said operating well; and computing, by said second artificial intelligence system (AI2) and based on the XRF and/or XRD measurements concerning said operating well, gamma radiation values for said operating well;

wherein the values of said one or more physical properties of said rocky formation crossed by said operating well are computed by said first artificial intelligence system (AI1) based on the gamma radiation values computed by said second artificial intelligence system (AI2) for said operating well and the values of said one or more drilling parameters of said operating well.

5. The method according to claim 1, wherein said first artificial intelligence system (AI1) comprises at least one of a random forest model, a support vector regression model, and a gradient boosting model.

6. The method according to claim 1, wherein said physical properties are divided into a first group and a second group, the physical properties of the first group are computed by said first artificial intelligence system (AI1), and the physical properties of the second group are computed by executing a further processing step based on one or more independent variables and/or one or more physical properties of the first group.

7. The method according to claim 1, wherein the values of physical properties computed by the first artificial intelligence system (AI1) are computed using a single artificial intelligence model.

8. The method according to claim 1, wherein said first artificial intelligence system (AI1) comprises a plurality of artificial intelligence subsystems (S1-S5), each artificial intelligence subsystem being dedicated to a subset of the physical properties computed by said first artificial intelligence system (AI1).

9. The method according to claim 1, wherein:

the independent variables (V1) of said first training dataset (TR1) comprise a lithological indication of said one or more rocky formations of said one or more training wells, and said operating data (OP) comprise a lithological indication (IND) of one or more rocky formations of said operating well.

10. The method according to claim 1, wherein one or more of said one or more dependent variables (V2) included in said first training dataset (TR1) are computed based on sonic logs and/or density logs concerning said one or more training wells.

11. A system for determining physical properties of rocky formations during drilling of an operating well, comprising:

a processor;
an input interface coupled to said processor; and
an output interface coupled to said processor,
wherein a first artificial intelligence system (AI1) is loaded in said processor, said first artificial intelligence system (AI1) being trained on a first training dataset (TR1) obtained from one or more training wells, said first training dataset (TR1) comprising:

independent variables (V1) comprising (i) at least one of X-ray fluorescence (XRF) measurements, X-ray diffraction (XRD) measurements, and gamma-ray measurements;

taken on cuttings or rocky formations of said one or more training wells, and (ii) one or more drilling parameters acquired during drilling of said one or more training wells;

one or more dependent variables (V2), comprising one or more physical properties of a rocky formation, depth-correlated with said independent variables;

wherein said processor is configured to:

acquire, via said input interface and in quasi-real-time during drilling of the operating well, operating data (OP) comprising values of XRF and/or XRD measurements taken on cuttings of said operating well and values of said one or more drilling parameters of said operating well;

compute, by said first artificial intelligence system (AI1) based on said operating data (OP), values of one or more physical properties (PP) of a rocky formation crossed by said operating well; and generate and output, via said output interface, one or more output signals (OUT) containing said computed values of said one or more physical properties (PP) for use in at least one of controlling or adjusting at least one of said one or more drilling parameters of said operating well and modelling a reservoir crossed by said operating well.

* * * * *